(12) United States Patent
Jeong

(10) Patent No.: US 7,199,946 B2
(45) Date of Patent: Apr. 3, 2007

(54) SYSTEMS CONFIGURED TO PROVIDE ILLUMINATION OF A SPECIMEN DURING INSPECTION

(75) Inventor: Hwan J. Jeong, Los Altos, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 11/145,829

(22) Filed: Jun. 6, 2005

(65) Prior Publication Data

US 2006/0274432 A1    Dec. 7, 2006

(51) Int. Cl.
G02B 17/00 (2006.01)
G01N 21/00 (2006.01)

(52) U.S. Cl. .................. 359/726; 359/730; 356/237.1
(58) Field of Classification Search ........ 359/726–731, 359/717, 710, 651; 356/237.1, 237.3, 237.4, 356/237.5

See application file for complete search history.

(56) References Cited

U.S. PATENT DOCUMENTS

| 2002/0015142 A1* | 2/2002 | Suzuki et al. ............... 355/71 |
| 2004/0095573 A1* | 5/2004 | Tsai et al. ............... 356/237.5 |
| 2005/0088630 A1* | 4/2005 | Sasaki ................... 353/99 |

* cited by examiner

Primary Examiner—Alicia Harrington
(74) Attorney, Agent, or Firm—Baker & McKenzie LLP

(57) ABSTRACT

Systems configured to provide illumination of a specimen during inspection are provided. One system includes catoptric elements configured to direct light from a light source to a line across the specimen at an oblique angle of incidence. The catoptric elements include positive and negative elements configured such that pupil distortions of the positive and negative elements are substantially canceled. Another system includes a dioptric element and a catoptric element. The dioptric element and the catoptric element are configured to direct light from a light source to a line across the specimen at an oblique angle of incidence. The dioptric and catoptric elements are also configured such that pupil distortions of the dioptric and catoptric elements are substantially canceled.

21 Claims, 6 Drawing Sheets

SYSTEMS CONFIGURED TO PROVIDE ILLUMINATION OF A SPECIMEN DURING INSPECTION

BACKGROUND OF THE INVENTION

1. Field of the Invention

This invention generally relates to systems configured to provide illumination of a specimen during inspection. Certain embodiments relate to a system that is configured to provide illumination of a specimen during inspection that includes elements configured such that pupil distortions of the elements substantially cancel.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

One common way to improve the detection of relatively small defects is to increase the sensitivity of an optical inspection system. One way to improve the sensitivity of an optical inspection system is to use oblique illumination for wafer defect detection, instead of normal illumination. Several different oblique illumination configurations have been devised and used. Among them, laser line illumination using cylindrical lenses is one of the most cost-effective illumination configurations currently available because it can provide both a long illumination field that is necessary for high throughput and high spatial resolution in the direction perpendicular to the illumination line that is necessary for high sensitivity.

However, there are difficulties in achieving both high resolution and a long field due to pupil distortion. The pattern of pupil distortion looks like a smile or a frown pattern at the entrance pupil plane depending on its sign. Pupil distortion can be tolerated if the energy distribution at the pupil plane is uniform. However, in reality, all practical pupils have sharp boundaries, and the Gaussian profile of a laser beam makes the energy distribution even less uniform. If the energy distribution at the entrance pupil is not uniform, pupil distortion can cause variations in resolution and light intensity along the illumination line. Such variations adversely affect wafer defect detection.

Glass cylindrical lenses are typically used for illumination line formation. The total power of the cylindrical lenses in an illumination system must be positive to focus a laser beam into a line. However, positive power glass lenses introduce positive pupil distortion. In addition, strong positive power lenses that are needed and commonly used for fine illumination line formation generate a large amount of positive pupil distortion. To cancel the positive pupil distortion, strong negative power lenses must be used. However, strong negative power lenses create total internal reflections or a large amount of high order aberrations that degrade the performance of the system to an unacceptable level. For this reason, currently used line illuminators do not use high power negative elements and unavoidably have a large amount of pupil distortion. The pupil distortion severely limits the length of the usable segment of the illumination line and consequently reduces throughput and prevents efficient use of laser power.

Accordingly, it would be advantageous to develop a system configured to provide oblique line illumination of a specimen for inspection applications that has relatively low, or even no, pupil distortion such that substantially uniform resolution and light intensity along the illumination line can be obtained thereby providing high sensitivity and such that substantially an entirety of the illumination line can be used for inspection thereby providing high throughput and highly efficient use of a light source.

SUMMARY OF THE INVENTION

The following description of various embodiments of systems configured to provide illumination of a specimen during inspection and systems configured to detect defects on a specimen is not to be construed in any way as limiting the subject matter of the appended claims.

One embodiment relates to a system configured to provide illumination of a specimen during inspection. The system includes catoptric elements configured to direct light from a light source to a line across the specimen at an oblique angle of incidence. The catoptric elements include positive and negative elements configured such that pupil distortions of the positive and negative elements are substantially canceled.

In one embodiment, the catoptric elements consist of one positive element and one negative element. In another embodiment, the positive and negative elements are cylindrical elements. In an additional embodiment, the positive and negative elements are configured such that the light from the light source is directed to the negative element and such that the negative element directs the light to the positive element.

In an embodiment, the positive and negative elements are arranged to provide a large working distance. In another embodiment, a distance from a surface of the positive element to a concentric axis of the system is about two times or more than a distance from a surface of the negative element to the concentric axis. In a further embodiment, the negative element is smaller than the positive element.

In one embodiment, the negative element has a larger power than the positive element. In some embodiments, surfaces of the positive and negative elements are substantially concentric or quasi-concentric. In another embodiment, a surface of one or more of the positive and negative elements is aspherized.

In an additional embodiment, a resolution and a light intensity along substantially an entirety of the line are substantially uniform. In a further embodiment, a numerical aperture of the system is greater than about 0.3. In some embodiments, the system also includes an aspheric glass plate positioned such that the light from the light source passes through the aspheric glass plate to the catoptric elements. Each of the embodiments of the system described above may be further configured as described herein.

Another embodiment relates to a system configured to provide illumination of a specimen during inspection. The system includes a dioptric element and a catoptric element. The dioptric element and the catoptric element are configured to direct light from a light source to a line across the specimen at an oblique angle of incidence. The dioptric and catoptric elements are also configured such that pupil distortions of the dioptric and catoptric elements are substantially canceled.

In one embodiment, the dioptric and catoptric elements have positive powers. In another embodiment, the dioptric and catoptric elements are cylindrical elements. In an additional embodiment, a resolution and a light intensity along substantially an entirety of the line are substantially uniform. Each of the embodiments of the system described above may be further configured as described herein.

An additional embodiment relates to a system configured to detect defects on a specimen. The system includes a light source configured to generate light. The system also includes catoptric elements configured to direct the light from the light source to a line across the specimen at an oblique angle of incidence. The catoptric elements include positive and negative elements configured such that pupil distortions of the positive and negative elements are substantially canceled. In addition, the system includes a detector configured to generate signals responsive to light from the line across the specimen. The signals can be used to detect the defects on the specimen. In one embodiment, the detector is configured to generate signals responsive to the light from substantially an entirety of the line across the specimen. Each of the embodiments of the system described above may be further configured as described herein.

A further embodiment relates to a system configured to detect defects on a specimen. The system includes a light source configured to generate light. The system also includes a dioptric element and a catoptric element. The dioptric element and the catoptric element are configured to direct the light from the light source to a line across the specimen at an oblique angle of incidence. The dioptric and catoptric elements are also configured such that pupil distortions of the dioptric and catoptric elements are substantially canceled. In addition, the system includes a detector configured to generate signals responsive to light from the line across the specimen. The signals can be used to detect the defects on the specimen. In one embodiment, the detector is configured to generate signals responsive to the light from substantially an entirety of the line across the specimen. Each of the embodiments of the system described above may be further configured as described herein.

BRIEF DESCRIPTION OF THE DRAWINGS

Other objects and advantages of the invention will become apparent upon reading the following detailed description and upon reference to the accompanying drawings in which.

Figure 1:
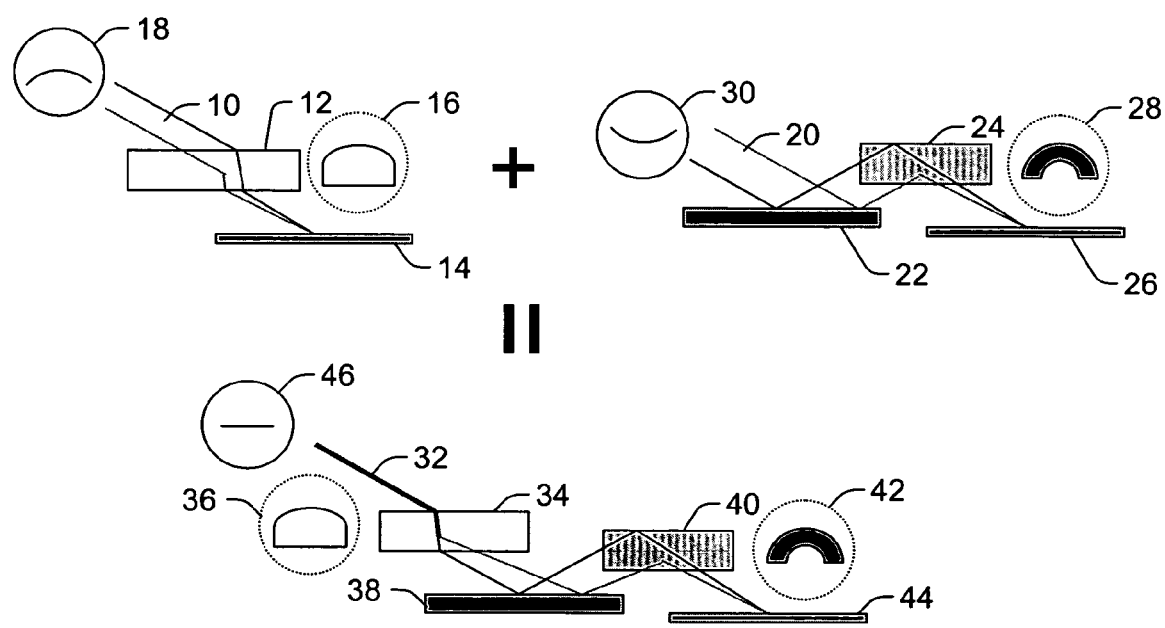
FIG. 1 is a schematic diagram illustrating a side view of different examples and an embodiment of a system that is configured to provide illumination of a specimen during inspection.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer or any other specimen that can be inspected using obliquely incident light.

As used herein, the term "wafer" generally refers to substrates formed of a semiconductor or non-semiconductor material. Examples of such a semiconductor or non-semiconductor material include, but are not limited to, mono crystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

The terms "aspherical" and "aspherize" are used herein with reference to optical elements having generally cylindrical surfaces, not spherical surfaces. Therefore, the terms "aspherical" and "aspherize" are not used herein to indicate that the optical elements have any surfaces that are generally spherical in nature. Instead, the terms "aspherical" and "aspherize" are used herein to describe the nature of a cylindrical surface of an optical element in place of the more correct terms "acylindrical" and "acylindrize" since these latter terms are not yet generally accepted optical terminologies.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates different examples and an embodiment of systems that are configured to provide illumination of a specimen during inspection. As shown in FIG. 1, one example of a system configured to provide illumination of a specimen during inspection directs light 10 from a light source (not shown) to dioptric element 12. Dioptric element 12 directs the light to specimen 14. Light 10 is directed to the specimen by dioptric element 12 at an oblique angle of incidence. Light 10 is also directed to the specimen in a line across the specimen. In this example, dioptric element 12 is a cylindrical lens having a positive power, as shown by cross-sectional profile 16 of the dioptric element. As shown in FIG. 1, this system has pupil distortion 18 presented at the entrance pupil plane (not shown) of the illumination system that resembles a frown shape in cross-section. In particular, the shape of the pupil distortion is defined by the ray fan shape that is traced from the specimen plane back to the entrance pupil plane.

The ray fan is generally defined herein using the following coordinate system. The x-direction is defined herein as the direction perpendicular to the paper. The y-direction is defined herein as the direction of the axes of revolution of cylindrical lens or mirror surfaces. The z-direction is defined herein as the direction perpendicular to the wafer surface. Thus, x-, y- and z-axes form an orthogonal coordinate system. Ray fan is a collection of rays that land on the same point at the wafer and have different magnitudes of x- or z-component of wave vector for different rays, but have the same magnitude of y-component of wave vector for all rays. Ray fan is uniquely defined if its landing or starting point is given.

As further shown in FIG. 1, another example of a system that is configured to provide illumination of a specimen during inspection directs light 20 from a light source (not shown) to flat mirror 22. Flat mirror 22 directs the light to catoptric element 24. Catoptric element 24 directs the light to specimen 26 at an oblique angle of incidence. Catoptric element 24 also directs the light to a line across the specimen. Catoptric element 24 is, in this example, a concave cylindrical mirror having a positive power, as shown by cross-sectional profile 28 of the catoptric element. As shown in FIG. 1, this system has pupil distortion 30 presented at the entrance pupil plane (not shown) of the illumination system that resembles a smile shape in cross-section.

The two examples of an illumination system described above form an illuminated line across the specimen. The illuminated line may be relatively sharp or "fine," but the sharpness will vary along the line due to the pupil distortion of the illumination system. In this manner, since the resolution of an inspection system, in which the illumination system is used, depends on the sharpness of the line, the resolution of the inspection system will vary across the line. In particular, since the line will lose sharpness across the line, the resolution across the line will be lower across some portions of the line than others. In addition, as the resolution decreases, the illuminated image formed on the specimen spreads out thereby decreasing light intensity of the illuminated image. In this manner, only the portion of the line across which the sharpness is relatively good can be used for inspection. In addition, a relatively large portion of the illuminated line may not be used for inspection purposes due to the pupil distortion thereby resulting in relatively inefficient use of the light source power.

In contrast, in one embodiment, a system configured to provide illumination of a specimen during inspection includes a dioptric element and a catoptric element. The dioptric element and the catoptric element are configured to direct light from a light source to a line across the specimen at an oblique angle of incidence. The dioptric and catoptric elements are also configured such that pupil distortions of the dioptric and catoptric elements are substantially canceled. In one such embodiment, the dioptric and catoptric elements have positive powers. In another such embodiment, the dioptric and catoptric elements are cylindrical elements.

One such embodiment of a system that is configured to provide illumination of a specimen during inspection of the specimen is shown in FIG. 1. As shown in FIG. 1, this embodiment of the system is configured to direct light 32 from a light source (not shown) to dioptric element 34. Dioptric element 34 is a cylindrical lens having a positive power, as shown in cross-section 36 of the dioptric element. Dioptric element 34 directs the light to flat mirror 38. Flat mirror 38 directs the light to catoptric element 40. As shown in cross-section 42, catoptric element 40 is a concave cylindrical mirror having a positive power. Catoptric element 40 directs the light to specimen 44 at an oblique angle of incidence.

As shown in FIG. 1, this system has pupil distortion 46 presented at the entrance pupil plane (not shown) of the illumination system that resembles a "poker face" in cross-section or, in other words, neither a smile nor a frown. In this manner, the embodiment of the illumination system shown in FIG. 1 has substantially no pupil distortion. The substantial elimination of the pupil distortion is a result of the substantial mutual cancellation of the pupil distortions of the positive power cylindrical lens (i.e., dioptric element 34) and the positive power cylindrical mirror (i.e., catoptric element 40).

In this manner, the embodiment of the illumination system shown in FIG. 1 will not have the disadvantages of the other examples of an illumination system shown in FIG. 1. In particular, the embodiment of the illumination system described above forms an illuminated line across the specimen. The illuminated line is relatively sharp, and the sharpness will not vary along the line since the system has substantially no pupil distortion. In this manner, since the resolution of the system depends on the sharpness of the line, the resolution of the system along substantially an entirety of the line is substantially uniform. In addition, since the resolution is substantially constant along the line, the illuminated image of the specimen remains substantially constant across the line. As such, a light intensity along substantially an entirety of the line is substantially uniform. In this manner, a relatively large portion of the illuminated line may be used for inspection purposes thereby resulting in relatively efficient use of the light source power and high throughput.

In each of the illumination systems shown in FIG. 1, the light source may be a laser light source or any other suitable light source known in the art. In addition, the light source may be selected based on the characteristics of the light that will be used for inspection of the specimen. The characteristics of the light (e.g., wavelength, polarization, intensity, etc.) may be selected based on the characteristics of the specimen and defects on the specimen that are to be detected by inspection.

The dioptric elements shown in FIG. 1 may be formed of any suitable refractive material known in the art. An appropriate refractive material may be selected based on characteristics of the light that will be used to illuminate the specimen. For instance, an appropriate refractive material may be selected based on the wavelength(s) of the light. Furthermore, the catoptric elements shown in FIG. 1 (including the flat mirrors) may be formed of any suitable material known in the art. Appropriate materials for the catoptric elements may also be selected based on the characteristics (e.g., wavelength) of the light. The powers and other characteristics of the dioptric and catoptric elements shown in FIG. 1 may be selected based on the particular configuration of the illumination system using any optical design methods and systems known in the art.

The embodiment shown in FIG. 1 provides one way to substantially eliminate pupil distortion thereby eliminating the problems that are caused by pupil distortion. As described above, the illumination system uses a combination of dioptric elements (e.g., glass lenses) and catoptric elements (e.g., mirrors). The dioptric and catoptric elements that are configured to provide substantial (or complete) elimination of the pupil distortion include cylindrical elements having positive powers. As such, the dioptric and catoptric elements of a cylindrical multi-element catadioptric line illumination system may have positive powers. In this case, the dioptric element creates positive pupil distortion, and the catoptric element generates negative pupil distortion that substantially cancels the positive pupil distortion. In this manner, the dioptric and catoptric elements of the cylindrical multi-element catadioptric line illumination system are configured to generate pupil distortions of opposite signs, which substantially cancel each other.

The embodiments described above provide a compact illuminator design. In addition, these embodiments provide suitable performance for relatively small numerical aperture systems (e.g., systems having a numerical aperture of less than about 0.3). However, for a large numerical aperture system (e.g., a system having a numerical aperture of greater than about 0.3) that is configured to illuminate a specimen with a fine illumination line, one or more of the dioptric and catoptric elements may be configured to have a relatively large amount of asphericity to reduce the amount of aberrations of the system.

Other embodiments described herein provide another manner in which the problems caused by pupil distortion can be substantially eliminated. In general, these embodiments include catoptric elements having opposite powers. Unlike the embodiment shown in FIG. 1, this type of illumination system can be used for relatively high numerical aperture systems without using one or more elements that have a relatively large amount of asphericity.

One embodiment of a system configured to provide illumination of a specimen during inspection includes catoptric elements configured to direct light from a light source to a line across the specimen at an oblique angle of incidence. The catoptric elements include positive and negative elements configured such that pupil distortions of the positive and negative elements are substantially canceled.

Figure 2:
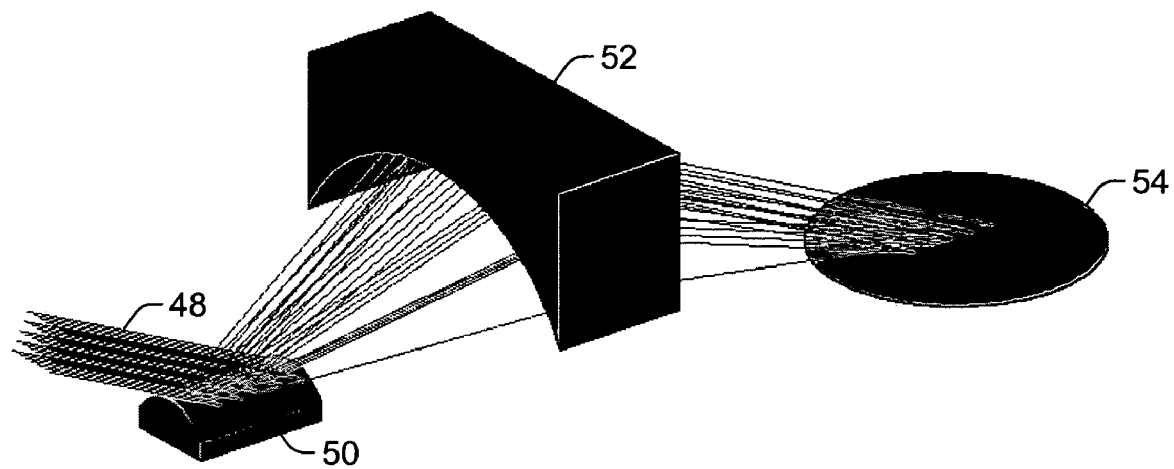
FIG. 2 is a schematic diagram illustrating a perspective view of one embodiment of a system configured to provide illumination of a specimen during inspection.
Figure 3:
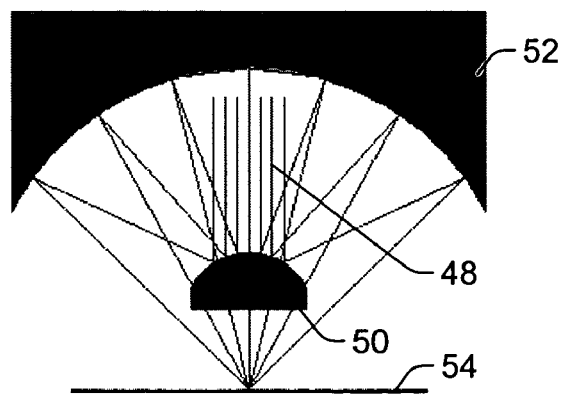
FIG. 3 is a schematic diagram illustrating an end view of the system of FIG. 2.

One such embodiment is illustrated in FIGS. 2 and 3. FIG. 3 is an end view of the system shown in FIG. 2. As shown in FIGS. 2 and 3, light 48 from a light source (not shown) is directed to catoptric element 50, which is a negative element. Catoptric element 50 directs the light to catoptric element 52, which is a positive element. Catoptric element 52 directs the light to a line across specimen 54 at an oblique angle of incidence. As shown in FIGS. 2 and 3, the positive and negative elements may be configured, in one embodiment, such that the light from the light source is directed to the negative element and such that the negative element directs the light to the positive element. In this manner, the input light beam first hits the smaller negative (convex) element and then the larger positive (concave) element.

Catoptric elements 50 and 52 include positive and negative elements configured such that pupil distortions of the positive and negative elements are substantially canceled. In particular, the negative element generates positive pupil distortion (i.e., the negative element acts as a frown generator), and the positive element generates pupil distortion of approximately the same amount but with the opposite sign (i.e., the positive element acts as a smile generator) to thereby substantially cancel the pupil distortion of the negative element. In this manner, the pupil distortion is mutually canceled by a negative power cylindrical mirror and a positive power cylindrical mirror.

In one embodiment, as shown in FIGS. 2 and 3, the positive and negative elements are cylindrical elements. In this manner, the illumination system may be configured as a cylindrical multi-element catoptric line illumination system. As further shown in FIGS. 2 and 3, the negative element is smaller than the positive element. In some embodiments, the catoptric elements of the embodiment shown in FIGS. 2 and 3 consist of one positive element and one negative element. In other words, the illumination system may include only two catoptric elements: one positive and one negative. In this manner, the illumination system may be configured as a cylindrical two-element catoptric line illumination system. However, as described further herein, the illumination system may include more than two catoptric elements. In any case, two catoptric elements of opposite powers can be configured as described herein to substantially eliminate the pupil distortion of the illumination system. Other catoptric elements (and/or dioptric elements) included in such a system may not be involved in the pupil distortion cancellation as long as these other elements do not themselves contribute to the pupil distortion.

Perfect mutual cancellation of pupil distortion is possible in the embodiments described herein by adjusting the power of each of the positive and negative elements and the distance between the two elements. In one embodiment, the negative element has a larger power than the positive element. The larger power of the negative element may provide matching of the magnitudes of the pupil distortions of the positive and negative elements. In an additional embodiment, a distance from a surface of the positive (concave) element to a concentric axis of the system is about two times or more than a distance from a surface of the negative (convex) element to the concentric axis. The concentric axis of the system may be generally defined as an axis that would be coaxial with an axis of catoptric element 50 if it was a completely cylindrical element (i.e., having the shape generally of a solid pipe). Therefore, in some embodiments, surfaces of the positive and negative elements are substantially concentric or quasi-concentric.

As further shown in FIGS. 2 and 3, the positive and negative elements are arranged to provide a large working distance (e.g., a working distance of about 50 mm or more). In particular, arranging the elements such that the negative (convex) element precedes the positive (concave) element along the optical path of the illumination system provides a large working distance for the system. The working distance of an illumination system may be generally defined as the distance between the last optical surface of the last element of the illumination system (i.e., the surface that is the last to reflect or refract the light beam along the optical path of the illumination system) and the specimen. In this manner, the illumination system shown in FIGS. 2 and 3 provides not only substantially zero pupil distortion, but also allows a relatively large working distance. A large working distance is advantageous such that mechanical conflict between the illumination system and other parts or subsystems of an inspection system (e.g., a relatively large lens used for signal collection) can be avoided.

The illumination system shown in FIGS. 2 and 3 will not have the disadvantages of the illumination system examples shown in FIG. 1. In particular, the embodiments of the illumination system described above form an illuminated line across the specimen. The illuminated line is relatively sharp, and the sharpness will not vary along the line since the system has substantially no pupil distortion. In this manner, since the resolution of the system depends on the sharpness of the line, the resolution of the system along substantially an entirety of the line is substantially uniform. In addition, since the resolution is substantially constant along the line, the illuminated image on the specimen remains substantially constant across the line. As such, a light intensity along substantially an entirety of the line is substantially uniform. In this manner, a relatively large portion of the illuminated line may be used for inspection purposes thereby resulting in relatively efficient use of the light source power. Moreover, all of the embodiments of the line illumination systems described herein provide a long illumination field (e.g., about 1 mm or more) that provides high throughput and high spatial resolution in the direction perpendicular to the illuminated line that provides high sensitivity. Furthermore, the catoptric elements of the illumination system will cause less polarization disturbance of the illumination than that which might be caused by dioptric elements.

The illumination system shown in FIGS. 2 and 3 may include a light source such as a laser light source or any other suitable light source known in the art. In addition, the light source may be selected based on the characteristics of the light that will be used for inspection of the specimen. The characteristics of the light (e.g., wavelength, polarization, intensity, etc.) may be selected based on the characteristics of the specimen and defects on the specimen that are to be detected by inspection.

Figure 4:
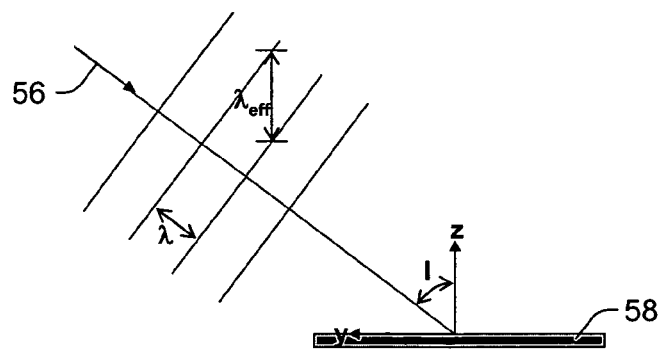
FIG. 4 is a schematic diagram illustrating the effective wavelength for oblique incidence systems.

The wavelength of the light that is used by the illumination system also affects the performance of an inspection system in which the illumination system is used. In oblique illumination inspection systems, the performance of the inspection system is dependent upon the wavelength of the light generated by the light source, but also the effective wavelength of the illumination. For instance, as shown in FIG. 4, wavelength, $\lambda$, of incident light 56 is different than the effective wavelength, $\lambda_{\textit{eff}}$, of the incident light and varies depending on the incidence angle, I, according to the following equation:

$$\lambda_{\textit{eff}} = \lambda/\cos(I).$$

Therefore, in one example, if an ultraviolet (UV) laser is used as the light source, which, for example, generates light at 355 nm, and light is directed to specimen 58 at an angle of incidence of 64 degrees, for example, then the effective wavelength is 810 nm. The width of the line that is imaged onto specimen 58 by an oblique illumination system depends on the effective wavelength according to the following equation:

$$\text{LineWidth} = 2\lambda_{\textit{eff}}/\pi NA.$$

Therefore, as the effective wavelength increases, the line width also increases thereby decreasing resolution. Although oblique illumination does result in an effective wavelength that is larger than the actual wavelength of the light and therefore a lower resolution, oblique illumination does provide higher sensitivity defect detection than normal illumination thereby offsetting the drawbacks of the lower resolution. In addition, the effects of lower resolution on the defect detection capability can be mitigated by selecting a light source that can generate light having the smallest possible (but also practical) wavelength for use in an illumination system of an inspection system.

The catoptric elements shown in FIGS. 2 and 3 may be formed of any suitable materials known in the art. Appropriate materials for the catoptric elements may also be selected based on its mechanical characteristics like hardness, polishability, etc. The power and other characteristics of the catoptric elements shown in FIGS. 2 and 3 may be selected as described above.

The illumination system shown in FIGS. 2 and 3 may be used in a relatively high numerical aperture inspection system. Therefore, the system shown in FIGS. 2 and 3 uses catoptric elements (i.e., mirrors) to provide a relatively high numerical aperture system with substantially no pupil distortion. For instance, in one embodiment, a numerical aperture of the system is greater than about 0.3. In one particular embodiment, a numerical aperture of the system may be about 0.7.

The illumination system shown in FIGS. 2 and 3 is substantially free of aberrations with a moderately high numerical aperture. In this manner, the surfaces of the catoptric elements may not be aspherized. However, this illumination system may exhibit high order aberrations at very high numerical apertures because of the relatively limited number of design variables that can be used to correct the aberrations. There are a couple of ways of reducing the high order aberrations at substantially high numerical aperture. One way to reduce the high order aberrations is to aspherize one or more of the surfaces of the catoptric elements. In one embodiment, a surface of one or more of the positive and negative elements is aspherized. Aspherizing one or more of the mirror surfaces is an attractive option because it does not increase the total number of elements of the illumination system and consequently allows easier system alignment and lower cost.

Figure 5:
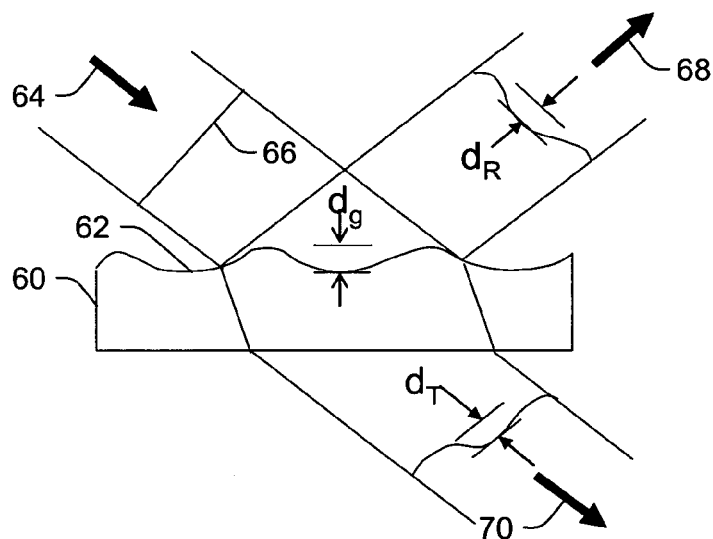
FIG. 5 is a schematic diagram illustrating the optical path difference (OPD) (or wavefront irregularity) sensitivity of light, reflected or transmitted by an element, to the surface figure error (irregularity) of the element.

Surface figure error of an optical element, which is not completely avoidable in optical fabrication processes, can distort the wavefront of the light emanating (e.g., reflected or transmitted) from the optical element. Surface figure error can be generally defined as a physical error in the surface of an optical element that may cause an error in the wavefront of the light emanating from the optical element. For instance, as shown in FIG. 5, element 60, which in this case can be either a mirror or a refractive element, has surface 62 that varies in height. The variation in the surface of the element may be caused, for instance, by marginalities in the process used to fabricate the element. The distance between the highest point of the surface and the lowest point of the surface can be defined as dg, as shown in FIG. 5.

Light 64 is incident on surface 62 at an oblique angle of incidence. Light 64 has substantially flat wavefront 66, as shown in FIG. 5. Light 68 that is reflected by element 60 and light 70 that is transmitted by element 60, however, do not have substantially flat wavefronts. Instead, the wavefronts of light 68 and light 70 have the same general non-planar shape as surface 62. The distance $d_R$ between the highest and lowest points of the wavefront of the reflected light and the distance $d_T$ between the highest and lowest points of the wavefront of the transmitted light are usually not equal to $d_g$. The ratios $d_R/d_g$ and $d_T/d_g$ describe how much of the surface figure error of element 60 is transferred to the wavefronts of the reflected and transmitted light. Preferably, the amount of variation in the wavefronts due to the surface figure error is relatively small. Therefore, small values of $d_R/d_g$ and $d_T/d_g$ indicate small distortion of the wavefront by element 60. In this manner, the ratio $d_R/d_g$ may be used to determine the distortion of the wavefront of light reflected by a catoptric element, and the ratio $d_T/d_g$ may be used to determine the distortion of the wavefront of light transmitted by a dioptric element.

A surface of a mirror may cause a substantial amount of error in the wavefront due to, for example, the reflection of the catoptric element. For example, if a mirror surface has a 1 µm bump formed thereon, the wavefront of the light reflected from the mirror may have up to a 2 µm bump corresponding to the bump on the mirror surface. Therefore, the surface figure error of a mirror may introduce non-negligible errors in the wavefront of light reflected from the mirror. However, the wavefront distortion sensitivity to surface figure error of a catoptric element is reduced by oblique incidence of light.

Figure 6:
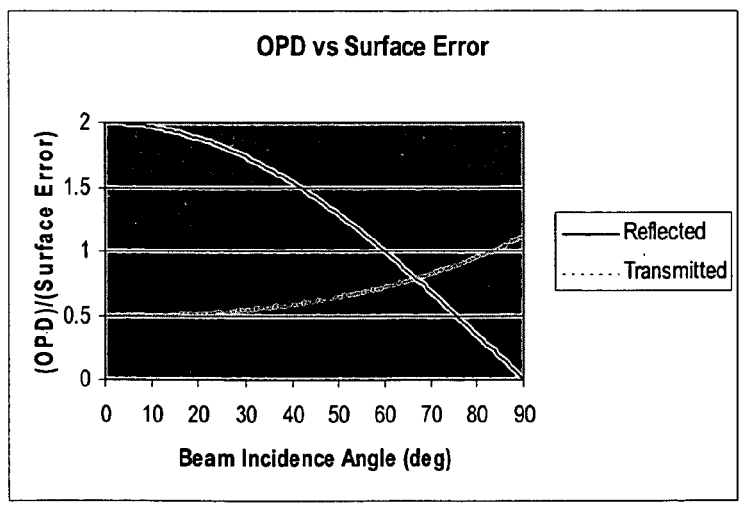
FIG. 6 is a graph illustrating the ratio of optical path difference (OPD) to surface figure error as a function of beam incidence angle for reflected and transmitted light.

For example, FIG. 6 illustrates the ratio of optical path difference (OPD) of a wavefront (i.e., wavefront error) of light reflected or transmitted by an optical element to surface figure error of the optical element as a function of beam incidence angle. A beam incidence angle of 0 degrees is normal incidence, and other beam incidence angles are oblique incidence angles. As shown in FIG. 6, as the beam incidence angle increases (e.g., from normal incidence to highly oblique incidence), the OPD/surface figure error ratio gradually increases for transmitted light (e.g., for a dioptric element). As further shown in FIG. 6, as the beam incidence angle increases, the OPD/surface figure error ratio decreases for reflected light (e.g., for a catoptric element). In addition, as the beam incidence angle increases, the OPD/surface figure error ratio decreases substantially for a catoptric element. Furthermore, as the beam incidence angle increases, the OPD/surface figure error ratio for a dioptric element and a catoptric element become about the same. As such, for oblique illumination, a mirror does not have to be highly corrected to achieve relatively low wavefront errors. Therefore, correcting aberrations by aspherizing a surface of one or more of the catoptric elements of the illumination system embodiments described herein is a substantially viable option for oblique incidence illumination.

One potential drawback to this approach may be the number of remaining available adjustments that can be made to the catoptric elements to compensate for surface figure error on other optical elements of the illumination system or residual misalignments. One approach that increases the number of compensations that can be made is to reduce the high order aberrations in the illumination system by adding an aspheric glass plate (an "acylinder") in front of the catoptric elements. In this case, the aspheric element in front of the catoptric elements can be used to not only eliminate design aberrations but also to compensate for small amounts of misalignments or surface figure error on the surfaces of the catoptric elements. In some embodiments, therefore, the illumination system includes an aspheric glass plate positioned such that the light from the light source passes through the aspheric glass plate to the catoptric elements. In either of these embodiments (apsherizing one or more of the catoptric elements or adding an aspheric glass plate), the amount of asphericity that will adequately reduce the high order aberrations is substantially smaller than the amount of asphericity that would be used for catadioptric illumination systems. In embodiments of the system that include an aspheric glass plate, a surface of one or more of the catoptric elements may or may not be aspherized.

Figure 7:
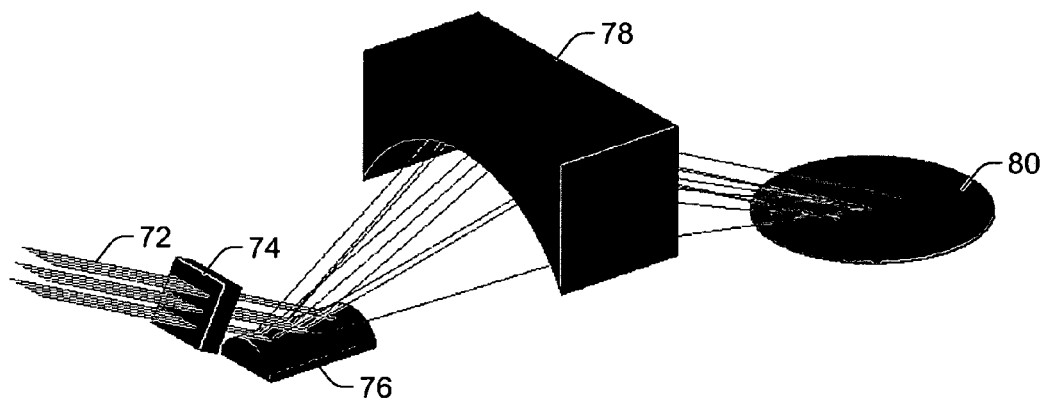
FIG. 7 is a schematic diagram illustrating a perspective view of another embodiment of a system configured to provide illumination of a specimen during inspection.
Figure 8:
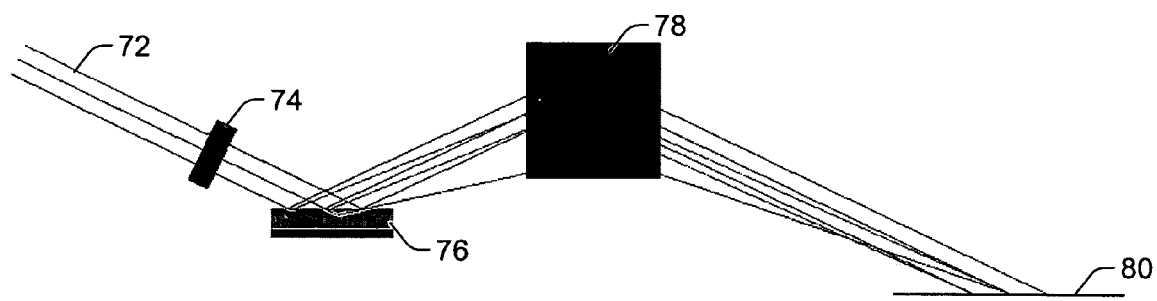
FIG. 8 is a schematic diagram illustrating a side view of the system of FIG. 7.
Figure 9:
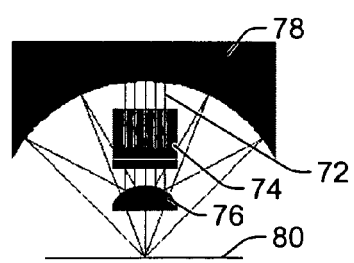
FIG. 9 is a schematic diagram illustrating an end view of the system of FIG. 7.

One embodiment of a system that is configured to illuminate a specimen during inspection, which includes an aspheric glass plate, is illustrated in FIGS. 7–9. FIG. 8 is a side view of the system of FIG. 7, and FIG. 9 is an end view of the system of FIG. 7. As shown in FIGS. 7–9, this embodiment of a cylindrical multi-element catoptric line illumination system includes an aspheric glass plate that precedes catoptric elements. In particular, as shown in FIGS. 7–9, light 72 from a light source (not shown) is directed to aspheric glass plate 74. Aspheric glass plate 74 may be configured as described above. In this embodiment, light 72 is directed to aspheric glass plate 74 at an approximately normal angle of incidence. Light that passes through the aspheric glass plate is directed to catoptric element 76, which is a negative (convex) element. Catoptric element 76 directs the light to catoptric element 78, which is a positive (concave) element. Catoptric element 78 directs the light to a line across specimen 80 at an oblique angle of incidence.

The embodiment and elements of the system shown in FIGS. 7–9 may be further configured as described above. For instance, catoptric elements 76 and 78 preferably include positive and negative elements configured such that pupil distortions of the positive and negative elements are substantially canceled. Catoptric elements 76 and 78 may be further configured as described above. Therefore, the embodiment shown in FIGS. 7–9 will have the same advantages as other embodiments described herein. In addition, the alignment of the system embodiment shown in FIGS. 7–9 can be easier because some residual misalignments of the catoptric elements can be compensated by an appropriate adjustment of the aspheric plate's position and rotation angle.

Figure 10:
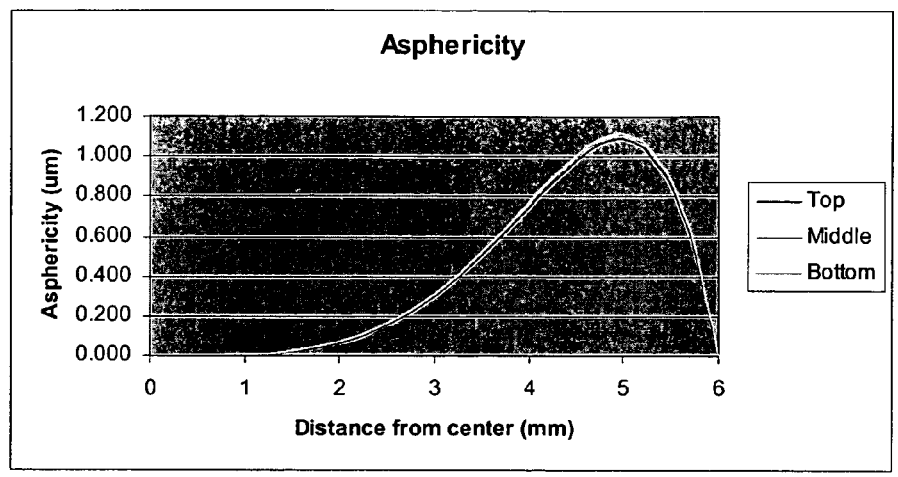
FIG. 10 is a graph illustrating asphericity versus distance from the center of an aspheric glass plate that may be included in the embodiments of the systems described herein.

Aspheric glass plate 74 may be formed of any suitable refractive material known in the art. In addition, the aspheric glass plate may be a slightly tapered asphere. In other words, the asphericity of the top and bottom portions of the aspheric glass plate may be different. However, in some instances, the difference in asphericity between the top and bottom portions of the aspheric glass plate may be relatively small and may be so small that the aspheric glass plate is essentially not tapered in actuality. In particular, FIG. 10 illustrates a graph of the asphericity (in µm) of the top, middle, and bottom portions of the aspheric glass plate as a function of distance from the center (in mm) of the aspheric glass plate. As shown in FIG. 10, the asphericity across the top, middle, and bottom portions of the aspheric glass plate are essentially the same. In addition, the differences between the asphericity of the different portions of the aspheric glass plate are smaller than the tolerance of many optical manufacturing processes. Therefore, in actuality, the aspheric glass plate may be essentially non-tapered.

Figure 11:
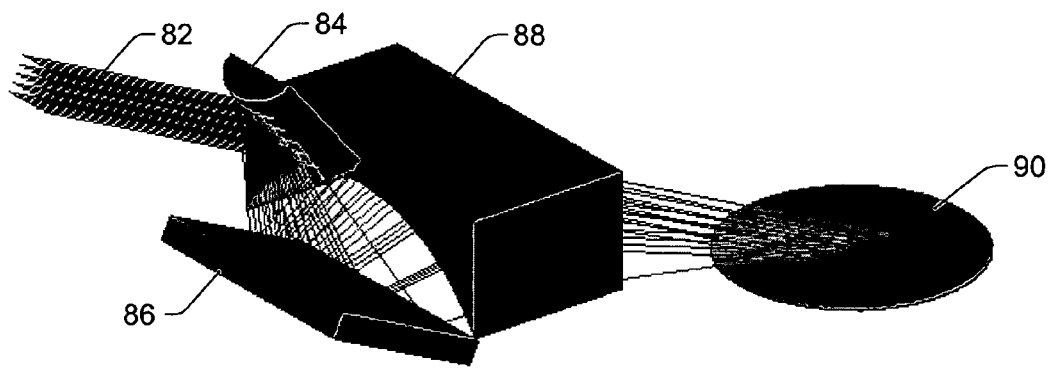
FIGS. 11 and 12 are schematic diagrams illustrating a perspective view of different embodiments of a system configured to provide illumination of a specimen during inspection.

FIG. 11 illustrates another embodiment of a system that is configured to provide illumination of a specimen during inspection. In this embodiment, light 82 from a light source (not shown) is directed to catoptric element 84, which is a negative (convex) element. Catoptric element 84 directs the light to flat glass plate 86. Flat glass plate 86 directs the light to catoptric element 88, which is a positive (concave) element. Catoptric element 88 directs the light to a line across specimen 90 at an oblique angle of incidence. In this manner, the input light beam first hits the smaller negative element and then the larger positive element. The input and output beam of the illuminator are in line with each other in this embodiment. This feature can facilitate the initial alignment of the input beam and the alignment of whole illuminator system to other optical systems such as a signal collection system.

The illumination system and elements of the system shown in FIG. 11 may be further configured as described herein. In particular, catoptric elements 84 and 88 include positive and negative elements configured such that pupil distortions of the positive and negative elements are substantially canceled. Therefore, the illumination system shown in FIG. 11 will have the same advantages as other embodiments described herein. In addition, the elements of the system of FIG. 11 are configured such that the optical path of the illumination system is folded, which may result in further compactness of the illumination system and no staggering of input and output beam lines. No staggering of input and output beam lines can make alignment of the illumination system to other optical systems easier. However, it is noted that the folded system has more elements to align, and it may be more difficult to align each part of this system compared to other system embodiments described herein.

Figure 12:
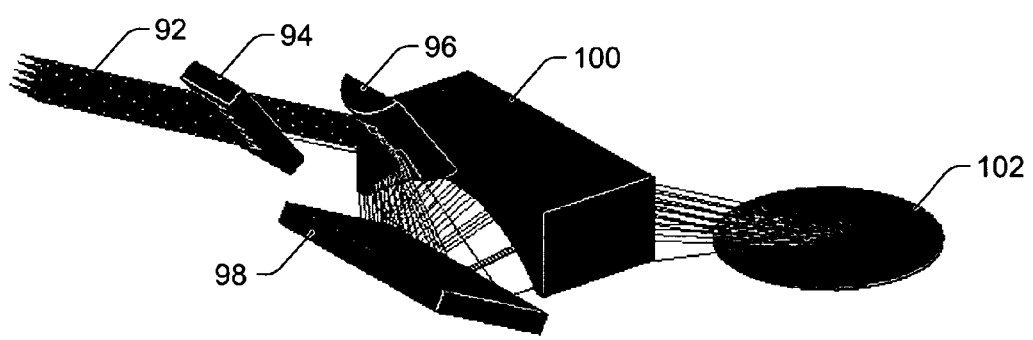

FIG. 12 illustrates an additional embodiment of a system that is configured to provide illumination of a specimen during inspection. In this embodiment, light 92 from a light source (not shown) is directed to aspheric glass plate 94, which may be configured as described above. In addition, due to the angle at which light 92 is incident on aspheric glass plate 94, the aspheric glass plate may have an anti-reflection (AR) coating formed thereon to reduce the amount of light 92 that is reflected from the input and output faces of the aspheric glass plate. Due to the tilt, the aspheric figure on glass plate 94 may not be tapered. Aspheric glass plate 94 directs the light to catoptric element 96, which is a negative (convex) element. Catoptric element 96 directs the light to folding mirror 98. Folding mirror 98 directs the light to catoptric element 100, which is a positive (concave) element. Catoptric element 100 directs the light to a line across specimen 102 at an oblique angle of incidence. In this manner, the input light beam first hits the smaller negative element and then the larger positive element. The input and output beam of the illuminator are in line with each other in this embodiment. This feature can facilitate the initial alignment of the input beam and the alignment of the illumination system to other optical systems such as a signal collection system.

The illumination system and elements of the system shown in FIG. 12 may be further configured as described herein. In particular, catoptric elements 96 and 100 include positive and negative elements configured such that pupil distortions of the positive and negative elements are substantially canceled. Therefore, the illumination system shown in FIG. 12 will have the same advantages as other embodiments described herein. In addition, the elements of the system of FIG. 12 are configured such that the optical path of the illumination system is folded, which may result in further compactness of the illumination system and no staggering of the input and output beam lines. No staggering of the input and output beam lines can make alignment of the whole illuminator as one unit easier. (Alignment of the optical system is generally done in two steps. The first step is part alignment in which each part is aligned relative to other parts. The second step is unit alignment in which whole system is aligned as single unit relative to other optical systems or mechanical parts.) However, it is noted that the folded system has more elements to align, and it may be more difficult to align each part of this system compared to other system embodiments described herein. The tilt of aspheric glass plate 94 can eliminate or reduce the tapering of aspheric figure across the plate. However, the anti-reflection coating on the surfaces of the aspheric glass plate will become more complex.

Figure 13:
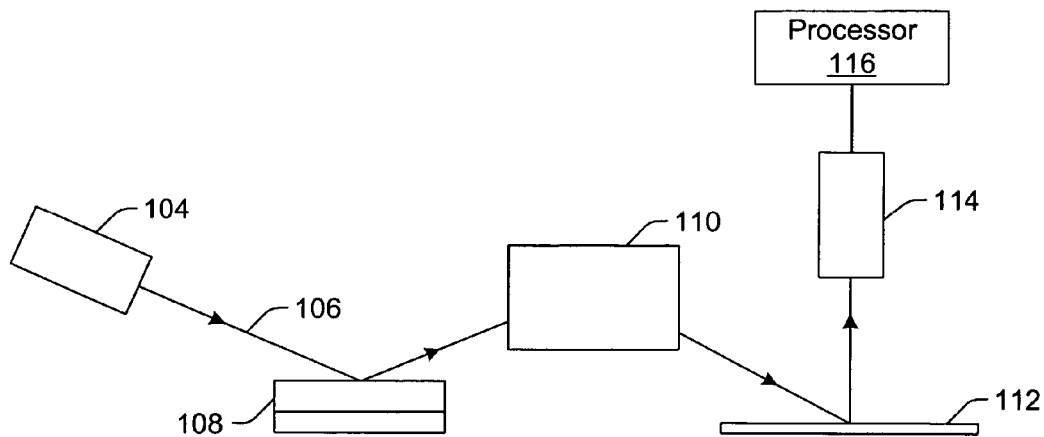
FIGS. 13 and 14 are schematic diagrams illustrating a side view of different embodiments of a system configured to detect defects on a specimen.

Another embodiment relates to a system configured to detect defects on a specimen. One such embodiment is illustrated in FIG. 13. As shown in FIG. 13, the system includes light source 104, which is configured to generate light 106. Light source 104 may include, for example, a laser configured to generate light having a wavelength of about 355 nm or any other suitable light source known in the art. The light source may also be selected as described herein.

The system also includes catoptric elements 108 and 110. Catoptric elements 108 and 110 are configured to direct light 106 from light source 104 to a line across specimen 112 at an oblique angle of incidence. Catoptric elements 108 and 110 include positive and negative elements. In particular, catoptric element 108 is a negative element, and catoptric element 110 is a positive element. The positive and negative elements are configured such that pupil distortions of the positive and negative elements are substantially canceled. Therefore, light source 104 and catoptric elements 108 and 110 form an illumination system of the inspection system. The illumination system and the catoptric elements of the illumination system may be further configured as described herein.

The system further includes detector 114, which is configured to generate signals responsive to light from the line across the specimen. The light from the line across the specimen may include reflected light, scattered light, diffracted light, or some combination thereof. The detector may include any suitable detector known in the art such as a 1-dimensional array of photosensitive elements. In some embodiments, the detector is configured to generate signals responsive to the light from substantially an entirety of the line across the specimen. For instance, as described above, because the sharpness of the line imaged on the specimen by the illumination system is substantially constant due to the substantial cancellation of the pupil distortion, the resolution of the system along substantially an entirety of the line is substantially uniform. In this manner, the light returned from a relatively large portion of the illuminated line on the specimen may be detected by the detector and used for inspection purposes thereby resulting in relatively efficient use of the light source power. In addition, since a relatively large portion of the illuminated line can be used for inspection, the system will have a relatively high throughput.

The signals generated by the detector can be used to detect the defects on the specimen. For instance, in some embodiments, the system may also include processor 116, which may be coupled to the detector in any manner known in the art (e.g., by a transmission medium or one or more electronic components (not shown)). The processor may be configured to receive the signals generated by the detector and to use the signals to detect defects on the specimen. The defects that may be detected using such a system include any type of defects that may be present on the specimen being inspected. The processor may be configured to use any method, technique, and/or algorithm known in the art to detect the defects. In addition, the processor may be configured to perform any other inspection-related functions known in the art (e.g., determining defect size, defect position, etc.). The processor may include any appropriate processing component known in the art such as a processor of a computer system. The system shown in FIG. 13 may be further configured as described herein.

Figure 14:
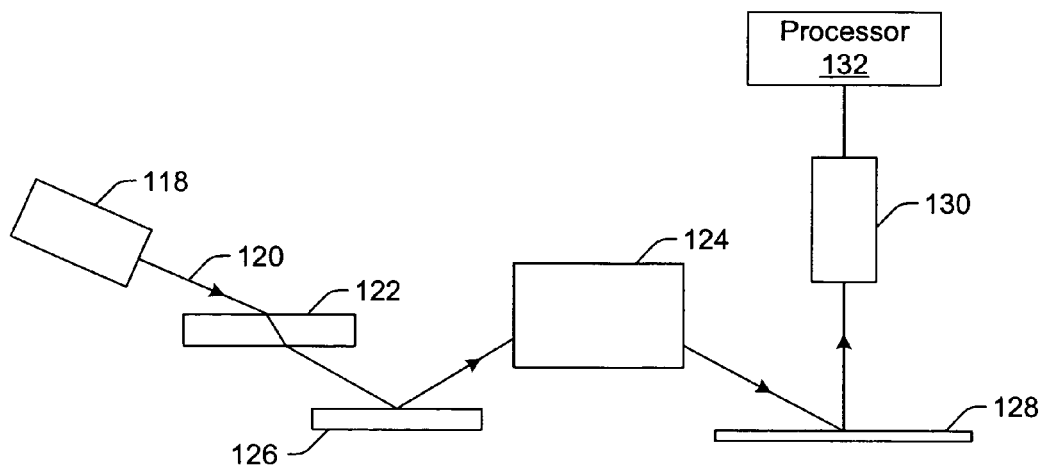

Another embodiment of a system that is configured to detect defects on a specimen is illustrated in FIG. 14. As shown in FIG. 14, the system includes light source 118, which is configured to generate light 120. Light source 118 may include, for example, a laser configured to generate light having a wavelength of about 355 nm or any other suitable light source known in the art. The light source may also be selected as described above.

The system also includes dioptric element 122 and catoptric element 124. Dioptric element 122 is configured to direct light 120 from light source 118 to flat mirror 126. Flat mirror 126 is configured to direct the light to catoptric element 124. Therefore, in combination, dioptric element 122 and catoptric element 124 are configured to direct light 120 from light source 118 to a line across specimen 128 at an oblique angle of incidence. The dioptric and catoptric elements are configured such that pupil distortions of the dioptric and catoptric elements are substantially canceled. Therefore, light source 118, dioptric element 122, catoptric element 124, and flat mirror 126 form an illumination system of the inspection system. The illumination system and the dioptric and catoptric elements of the illumination system may be further configured as described herein.

The system further includes detector 130, which is configured to generate signals responsive to light from the line across the specimen. The light from the line across the specimen may include reflected light, scattered light, diffracted light, or some combination thereof. The detector may include any suitable detector known in the art such as a 1-dimensional array of photosensitive elements. In some embodiments, the detector is configured to generate signals responsive to the light from substantially an entirety of the line across the specimen. For instance, as described above, because the sharpness of the line imaged on the specimen by the illumination system is substantially constant due to the substantial cancellation of the pupil distortion, the resolution of the system along substantially an entirety of the line is substantially uniform. In this manner, the light returned from a relatively large portion of the illuminated line on the specimen may be detected by the detector and used for inspection thereby resulting in relatively efficient use of the light source power. In addition, since a relatively large portion of the illuminated line can be used for inspection, the system will have a relatively high throughput.

The signals generated by the detector can be used to detect the defects on the specimen. For instance, in some embodiments, the system may also include processor 132, which may be configured as described above. The system shown in FIG. 14 may be further configured as described herein.

Although different embodiments of an inspection system are shown in FIGS. 13 and 14 in which the illumination system embodiments described herein may be used, it is to be understood that the illumination system embodiments may be included in any optical inspection system that uses, or can be configured to use, oblique incidence illumination to detect defects on a specimen. Examples of commercially available inspection systems in which the illumination system embodiments described herein may be used include the AIT family of tools and the Puma 9000 Series of tools, which are commercially available from KLA-Tencor, San Jose, Calif.

Further modifications and alternative embodiments of various aspects of the invention may be apparent to those skilled in the art in view of this description. For example, systems configured to provide illumination of a specimen during inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to provide illumination of a specimen during inspection, comprising catoptric elements configured to direct light from a light source to a line across the specimen at an oblique angle of incidence, wherein the catoptric elements comprise positive and negative elements configured such that pupil distortions of the positive and negative elements are substantially canceled.

2. The system of claim 1, wherein the catoptric elements consist of one positive element and one negative element.

3. The system of claim 1, wherein the positive and negative elements are cylindrical elements.

4. The system of claim 1, wherein the positive and negative elements are further configured such that the light from the light source is directed to the negative element and such that the negative element directs the light to the positive element.

5. The system of claim 1, wherein the positive and negative elements are arranged to provide a large working distance.

6. The system of claim 1, wherein a distance from a surface of the positive element to a concentric axis of the system is about two times or more than a distance from a surface of the negative element to the concentric axis.

7. The system of claim 1, wherein the negative element is smaller than the positive element.

8. The system of claim 1, wherein the negative element has a larger power than the positive element.

9. The system of claim 1, wherein surfaces of the positive and negative elements are substantially concentric or quasi-concentric.

10. The system of claim 1, wherein a surface of one or more of the positive and negative elements is aspherized.

11. The system of claim 1, wherein a resolution and a light intensity along substantially an entirety of the line are substantially uniform.

12. The system of claim 1, wherein a numerical aperture of the system is greater than about 0.3.

13. The system of claim 1, further comprising an aspheric glass plate positioned such that the light from the light source passes through the aspheric glass plate to the catoptric elements.

14. A system configured to provide illumination of a specimen during inspection, comprising a dioptric element and a catoptric element, wherein the dioptric element and the catoptric element are configured to direct light from a light source to a line across the specimen at an oblique angle of incidence, and wherein the dioptric and catoptric elements are configured such that pupil distortions of the dioptric and catoptric elements are substantially canceled.

15. The system of claim 14, wherein the dioptric and catoptric elements have positive powers.

16. The system of claim 14, wherein the dioptric and catoptric elements are cylindrical elements.

17. The system of claim 14, wherein a resolution and a light intensity along substantially an entirety of the line are substantially uniform.

18. A system configured to detect defects on a specimen, comprising:
  a light source configured to generate light;
  catoptric elements configured to direct the light from the light source to a line across the specimen at an oblique angle of incidence, wherein the catoptric elements comprise positive and negative elements configured such that pupil distortions of the positive and negative elements are substantially canceled; and
  a detector configured to generate signals responsive to light from the line across the specimen, wherein the signals can be used to detect the defects on the specimen.

19. The system of claim 18, wherein the detector is further configured to generate signals responsive to the light from substantially an entirety of the line across the specimen.

20. A system configured to detect defects on a specimen, comprising:
  a light source configured to generate light;
  a dioptric element and a catoptric element, wherein the dioptric element and the catoptric element are configured to direct the light from the light source to a line across the specimen at an oblique angle of incidence, and wherein the dioptric and catoptric elements are configured such that pupil distortions of the dioptric and catoptric elements are substantially canceled; and
  a detector configured to generate signals responsive to light from the line across the specimen, wherein the signals can be used to detect the defects on the specimen.

21. The system of claim 20, wherein the detector is further configured to generate signals responsive to the light from substantially an entirety of the line across the specimen.

* * * * *